United States Patent
DiMambro et al.

(10) Patent No.: US 8,371,173 B1
(45) Date of Patent: *Feb. 12, 2013

(54) ULTRASONIC PROBE DEPLOYMENT DEVICE FOR INCREASED WAVE TRANSMISSION AND RAPID AREA SCAN INSPECTIONS

(75) Inventors: Joseph DiMambro, Placitas, NM (US); Dennis P. Roach, Albuquerque, NM (US); Kirk A. Rackow, Albuquerque, NM (US); Ciji L. Nelson, Albuquerque, NM (US); Cameron J. Dasch, Boomfield Hills, MI (US); David G. Moore, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/237,520

(22) Filed: Sep. 20, 2011

Related U.S. Application Data

(63) Continuation of application No. 12/401,321, filed on Mar. 10, 2009, now Pat. No. 8,087,298.

(51) Int. Cl.
*G01N 29/00* (2006.01)
(52) U.S. Cl. .......................................... 73/629; 73/644
(58) Field of Classification Search .................... 73/629, 73/628, 641, 644
See application file for complete search history.

(56) References Cited

U.S. PATENT DOCUMENTS

| | | | |
|---|---|---|---|
| 4,183,249 A | 1/1980 | Anderson | |
| 4,290,612 A * | 9/1981 | Frosch et al. | 277/345 |
| 4,472,975 A | 9/1984 | Beck et al. | |
| 5,060,201 A | 10/1991 | Ishikawa et al. | |
| 5,255,684 A * | 10/1993 | Rello | 600/463 |
| 5,343,109 A | 8/1994 | Mockl | |
| 5,426,980 A * | 6/1995 | Smith | 73/644 |
| 5,450,851 A * | 9/1995 | Hancock | 600/462 |
| 5,469,744 A | 11/1995 | Patton et al. | |
| 5,494,038 A | 2/1996 | Wang et al. | |
| 5,729,508 A | 3/1998 | Baker et al. | |
| 5,785,541 A * | 7/1998 | Best et al. | 439/164 |
| 5,814,731 A | 9/1998 | Alexander et al. | |
| 6,117,084 A * | 9/2000 | Green et al. | 600/459 |
| 6,298,727 B1 | 10/2001 | Fleming et al. | |
| 6,481,290 B1 | 11/2002 | MacInnis et al. | |
| 6,578,424 B1 * | 6/2003 | Ziola et al. | 73/632 |
| 6,733,457 B2 | 5/2004 | Flesch et al. | |
| 6,938,488 B2 * | 9/2005 | Diaz et al. | 73/597 |
| 6,948,369 B2 | 9/2005 | Fleming et al. | |
| 7,284,434 B1 | 10/2007 | Fleming | |
| 7,694,569 B2 | 4/2010 | McGrath et al. | |
| 7,926,344 B1 | 4/2011 | Hyde et al. | |
| 8,166,823 B2 * | 5/2012 | Lam et al. | 73/622 |
| 8,174,930 B2 * | 5/2012 | LaWhite et al. | 367/90 |

OTHER PUBLICATIONS

Hsu, D. K. et al, "Detection and Imaging of Corrosion Around Wing Skin Fasteners Using the Dripless Bubbler Ultrasonic Scanner" SPIE vol. 3397. (1998), pp. 32-38.
Hsu. D.K. et al., "Nondestructive Evaluation of Repairs on Aircraft Composite Structures", SPIE vol. 4336, (2001), pp. 100-107.

\* cited by examiner

*Primary Examiner* — J M Saint Surin
(74) *Attorney, Agent, or Firm* — Daniel J. Jenkins

(57) ABSTRACT

An ultrasonic probe deployment device in which an ultrasound-transmitting liquid forms the portion of the ultrasonic wave path in contact with the surface being inspected (i.e., the inspection surface). A seal constrains flow of the liquid, for example preventing the liquid from surging out and flooding the inspection surface. The seal is not rigid and conforms to variations in the shape and unevenness of the inspection surface, thus forming a seal (although possibly a leaky seal) around the liquid. The probe preferably is held in place to produce optimum ultrasonic focus on the area of interest. Use of encoders can facilitate the production of C-scan area maps of the material being inspected.

30 Claims, 6 Drawing Sheets

ULTRASONIC PROBE DEPLOYMENT DEVICE FOR INCREASED WAVE TRANSMISSION AND RAPID AREA SCAN INSPECTIONS

RELATED APPLICATIONS

This application is a continuation of application Ser. No. 12/401,321, filed Mar. 10, 2009, now allowed, entitled "ULTRASONIC PROBE DEPLOYMENT DEVICE FOR INCREASED WAVE TRANSMISSION AND RAPID AREA SCAN INPSECTIONS, for which priority is claimed and whose disclosure is incorporated by reference in its entirety.

STATEMENT REGARDING FEDERALLY SPONSORED RESEARCH OR DEVELOPMENT

The United States Government has certain rights in this invention pursuant to Department of Energy Contract No. DE-AC04-94AL85000 with Sandia Corporation.

FIELD OF THE INVENTION

This invention relates generally to ultrasonic inspection of materials, including for example bonded joints that can have uneven surfaces, and narrow joint width.

BACKGROUND OF THE INVENTION

As an example, advances in structural adhesives have permitted engineers to contemplate the use of bonded joints in areas that have long been dominated by mechanical fasteners and welds. The deployment of bonded joints generally requires the use of sensitive nondestructive inspection techniques to ensure the continued integrity of the bond joint.

For example, the use of adhesive bonding in automobile bodies is increasing every year for various reasons. However, current quality control of these joints relies primarily on the robust control of the adhesive preparation and application. These controls may include machine vision inspection of the applied adhesive bead. However, there is no practical method currently available to test the overall quality of the final joints other than destructive testing. Nondestructive testing would reduce this scrap, increase the rate of testing, and improve the reliability of adhesive joints. Within the automotive manufacturing arena, nondestructive inspections would be beneficial in the body shop before the adhesive is cured. Here, discrepant joints could be repaired. However, inspections would also be beneficial at the end of the assembly line to ensure the quality of the entire assembled, cured, and painted product. Nondestructive inspections are also seen as a major cost savings for accelerating engineering and environmental testing, ramp-up to production, and monitoring the long term performance of the joints.

In the automobile example, individual adhesive joints can be long (approaching 1 m) and relatively narrow (typically 10-25 mm). Moreover, the sum total of the adhesive joints may be over 100 m in length in a single vehicle. This requires a practical inspection device that can transverse long bead or flange structures at speeds preferably over 1 m/min. To ensure the adhesive joint strength, the bead width, thickness, location on flanges, and the state of cure are all desirable inspection features.

In the automobile example, access to the back side of the material being inspected is not always possible due to geometry constraints and other obstructions. This limits the applicability of some nondestructive techniques, for example through-transmission ultrasound (since the receiving transducer requires back side access) or radiography (since the digital panel or film requires back side access). While pulsed thermography can be a single sided technique, an emissive coating must usually be applied to the surface of metal parts prior to an inspection. The coating residue must be completely removed before the automobile is painted which adds complexity, risk, and cost to the inspection process. Eddy current inspection is also not viable because the adhesive is nonconductive.

One possible technology for nondestructive inspection is pulse-echo ultrasound. This uses short bursts of high frequency sound waves that are introduced into the material for the detection of surface and subsurface flaws in the material (e.g., composites, metals, plastics, ceramics, etc.). The ultrasonic waves are generated by an ultrasonic probe (transmitter). The ultrasonic wave interacts with the material and the resulting wave is detected by an ultrasonic probe (receiver). Water, gel or other fluids are typically applied between the probe(s) and the material to couple the sound since it cannot travel as well through air. If sufficient coupling is achieved, the ultrasonic waves travel through the material with some attenuations and are reflected at interfaces. The reflected beam is displayed on an instrument and then analyzed to define the presence and location of adhesive and flaws (e.g., disbonds). Complete reflection, partial reflection, scattering, or other detectable effects on the ultrasonic waves can be used as the basis of flaw detection. In addition to wave reflection, the time of transit through the test piece can be used to assess adhesive bond-line thickness.

For good results, it is important to maintain good coupling along the entire ultrasonic wave path from transmitter to receiver. This can be a significant challenge when the probe encounters complex curvature and uneven inspection surfaces, for example from spot welds and spot weld expulsions which are common in automobile design and production. In addition, if a fluid is used to enhance the coupling, for automotive applications, the fluid couplant preferably does not leave a residue (such as those left by gels), is not toxic, and does not require large drain or tank systems.

Thus, there is a need for ultrasound deployment devices that can accommodate the rapid inspection of complex curvatures and shapes, and/or uneven inspection surfaces. There is a further need for such devices that do not require access to the back side of the material being inspected. In addition, there is a need for such devices to be small enough that they can be used to inspect narrow flanges or joints and fit into small hard to reach or confined areas, some of which can be vertical or inverted. There is a further need for devices that provide for reduced leakage/loss of fluid couplants while minimizing fluid turbulence within the device that can degrade the ultrasonic signal. It is also desirable to produce two-dimensional images of the inspection area (e.g. C-Scan images) as opposed to one-dimensional inspection methods (e.g. A or B-scan imaging).

SUMMARY OF THE INVENTION

The present invention overcomes the limitations of the prior art by providing ultrasonic probe deployment device in which an ultrasound-transmitting liquid forms the portion of the ultrasonic wave path in contact with the surface of the material being inspected (i.e., the inspection surface). A seal constrains flow of the liquid, for example preventing the liquid from gushing out and flooding the inspection surface. The seal is not rigid and conforms to variations in the shape and unevenness of the inspection surface, thus forming a seal around the liquid. The seal can comprise a compliant gasket subjected to a pre-determined amount of compression thereby maximizing its effectiveness.

In an example embodiment, such a device includes a housing, an ultrasonic probe attached to the housing, a liquid supply port and a conforming seal. For various applications, the housing preferably is shaped and sized small enough to follow surface contours and to inspect tight areas like narrow flanges and corners. The housing preferably is portable so that it can be moved, either manually or robotically.

The overall ultrasonic system includes a transmitter and a receiver. In pulse-echo ultrasonics, the same probe (i.e., same transducer element(s)) acts as both the transmitter and the receiver. In other types of ultrasonics, different probes (i.e., different transducer elements) can be used as transmitter and receiver. Ultrasonic waves follow an ultrasonic wave path from the transmitter to an inspection site on the inspection surface and then to the receiver. A volume of ultrasound-transmitting non-viscous liquid (e.g. water) extends along a portion of the ultrasonic wave path that includes the inspection site. The liquid is contained in a cavity formed by the housing and the seal. The seal is attached to the bottom side of the housing and forms a seal around the inspection site, thus constraining flow of the liquid onto the inspection surface. The seal conforms to unevenness in the inspection surface, although it may not be perfectly conforming and may not be perfectly sealing.

The device can have many variations. For example, the ultrasonic probe can be a simple ultrasonic array or a phased ultrasonic array, a linear array probe, a single transducer probe, or other type of probe that is electronically scanned along one dimension. If an area scan is desired, the device can be designed to move in the perpendicular direction (which shall be referred to as the scan direction). An encoder records and relates the position of the device as it is moved along the scan direction. This allows for the production of C-Scan type of color-coded maps that show the presence and allow the measurement of flaws and defects, or otherwise show changes in the material. For example, roller guides (e.g. wheels) can be used to facilitate movement along the scan direction and can also be used in encoding the position of the device. The roller guides can retard any undesired lateral motion (e.g. in the index direction). In other designs, area ultrasonic arrays might also be used to increase the scanning speed or to provide redundant measurements. In other designs, the ultrasonic probe can be a spot probe that is mechanically moved in two dimensions, optionally with a corresponding two-dimensional position encoder. Various position encoders such as rotary wheel encoders, string encoders, or linear variable differential transformers (LVDT) can be used. Encoder devices incorporated into the probe holder assembly can allow for complete area mapping of an inspection surface. This facilitates the production of C-scan color-coded maps that show the presence of flaws or other changes in the material.

In further examples, the device contains a permeable membrane that divides the cavity containing the liquid into a non-contact chamber and a contact chamber. The contact chamber includes the inspection site. The liquid supply port provides liquid to the non-contact chamber, and the permeable membrane permits flow of the liquid from the non-contact chamber to the contact chamber. The non-contact chamber preferably has a greater volume than the contact chamber and the ultrasonic wave path preferably is longer in the non-contact chamber than in the contact chamber. In this way, the majority of liquid resides in the non-contact chamber, which is better contained than the contact chamber. One example of a permeable membrane is a membrane constructed of non-porous material with perforations. Flow between the two chambers can be adjusted by changing the quantity or number of perforations as well as the area or size of each perforation.

In other aspects, vacuum port(s) may be used to remove excess liquid that flows onto the inspection surface. In some aspects of the invention, the sealing gasket can separate areas to which liquid is flowing onto the surface from areas where the fluid is removed by the vacuum port(s). In additional aspects of the invention, the seal can include channels (e.g. passageways) between these areas to provide for a controlled/reduced amount of fluid flow in the ultrasonic inspection device, thereby decreasing turbulence and increasing the fidelity of the ultrasonic inspection signal. In another aspect, the housing can be made transparent so that the volume of liquid can be directly observed. Preferably, the flow of liquid through the cavity does not form bubbles or air pockets, as these will adversely affect propagation of the ultrasonic waves.

Using the one-sided inspection of adhesive bonds in automobiles as an example, the ultrasonic probe deployment device preferably has a size and shape suited for its intended task. For example, if the device is to be used to inspect long bonds that run along curved automobile parts, then it preferably is small enough and narrow enough to navigate this geometry. In various implementations, the device is long and narrow—not wider than 0.70" in some designs, and not wider than 1.50" in alternate designs. For automotive inspections, the device preferably will be approximately as wide as the adhesively bonded flanges, which currently typically range from 10 to 25 mm wide. While for an ideal inspection the device would span the entire flange width, it may be advantageous for the device only to be as wide as the minimum required bead width. If the device is too narrow, it may be unstable and may tilt as it travels along the surface. To inspect adhesive bonds at the bottom of "hat" sections, the device must be narrower than the channel width. The length of the device preferably is short relative to the adhesive bond length and the surface curvature along the bead but long enough to have a stable conformance to the surface. For current automobile applications, the device preferably is longer than 10 mm but shorter than 100 mm. The height of the device above the inspection surface preferably is short in order to improve its accessibility to confined areas and its stability. The height should be large enough so that the ultrasonic beam is focused approximately at the location of the material being inspected.

In other aspects of the invention, the width of the device can be minimized to accommodate narrow adhesive bonds by incorporating ultrasonic transducers of the near wall design, eliminating vacuum ports from the sides of the probe deployment device, and moving wheels, encoders etc. to the front and back of the device's body (i.e. not on the sides). By these methods, small and compliant devices can be realized that allow for rapid inspection of bonded joints and further provide output representative of two dimensional images (i.e. C-Scan) that can be readily and rapidly interpreted by an inspector. By incorporating phased-array ultrasonic probes (e.g. steerable wave) the invention further provides devices that can inspect (e.g. "see") bonded joints that may not be directly accessible under the probe head itself (e.g. inspecting the bond between a "wall" member and a "floor" member, while moving the probe on the floor and along the wall).

Other aspects of the invention include components of the devices described above, and systems using these devices. For example, another aspect is the devices described above but without the ultrasonic probe itself. This will be referred to as an ultrasonic probe support assembly. Other aspects include methods corresponding to all of the foregoing.

BRIEF DESCRIPTION OF THE DRAWINGS

The invention has other advantages and features which will be more readily apparent from the following detailed description of the invention and the appended claims, when taken in conjunction with the accompanying drawings, in which:

The figures depict embodiments of the present invention for purposes of illustration only, and are not necessarily drawn to scale. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENTS

Figure 1:
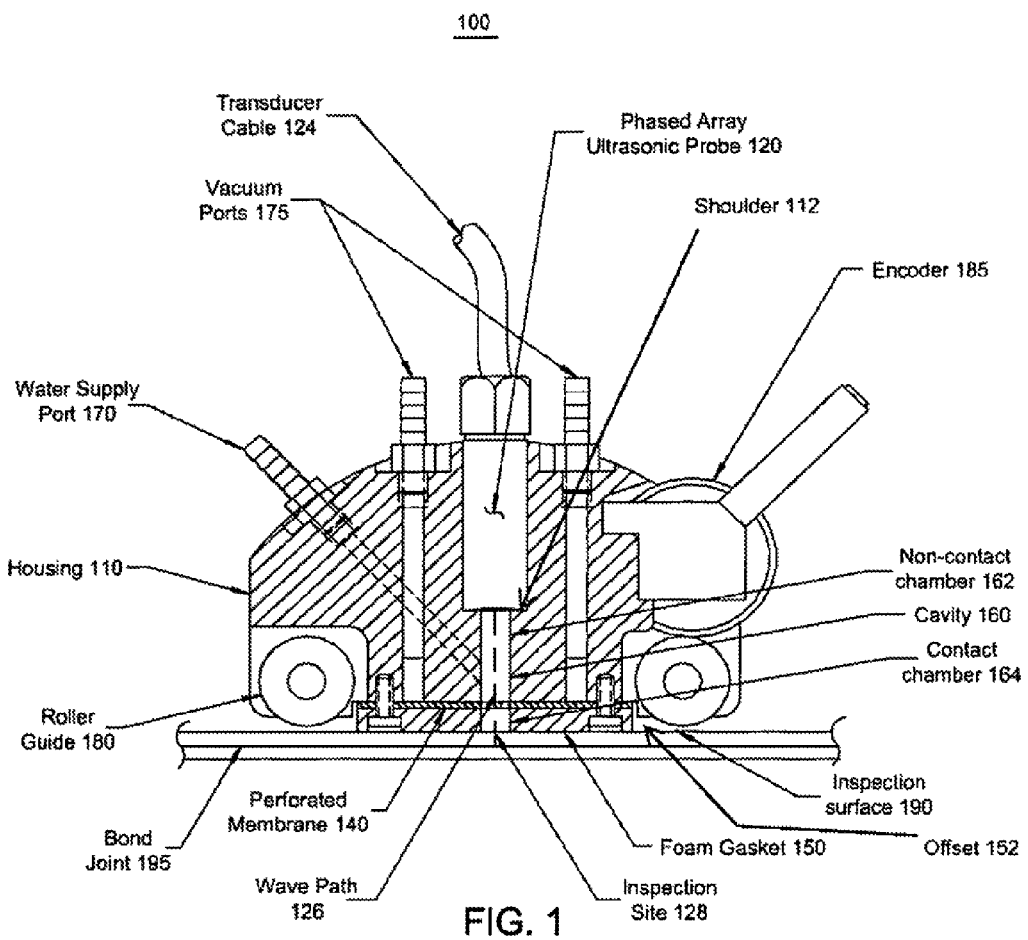
FIG. 1 is a cross-section view of an ultrasonic probe deployment device according to the invention.
Figure 2:
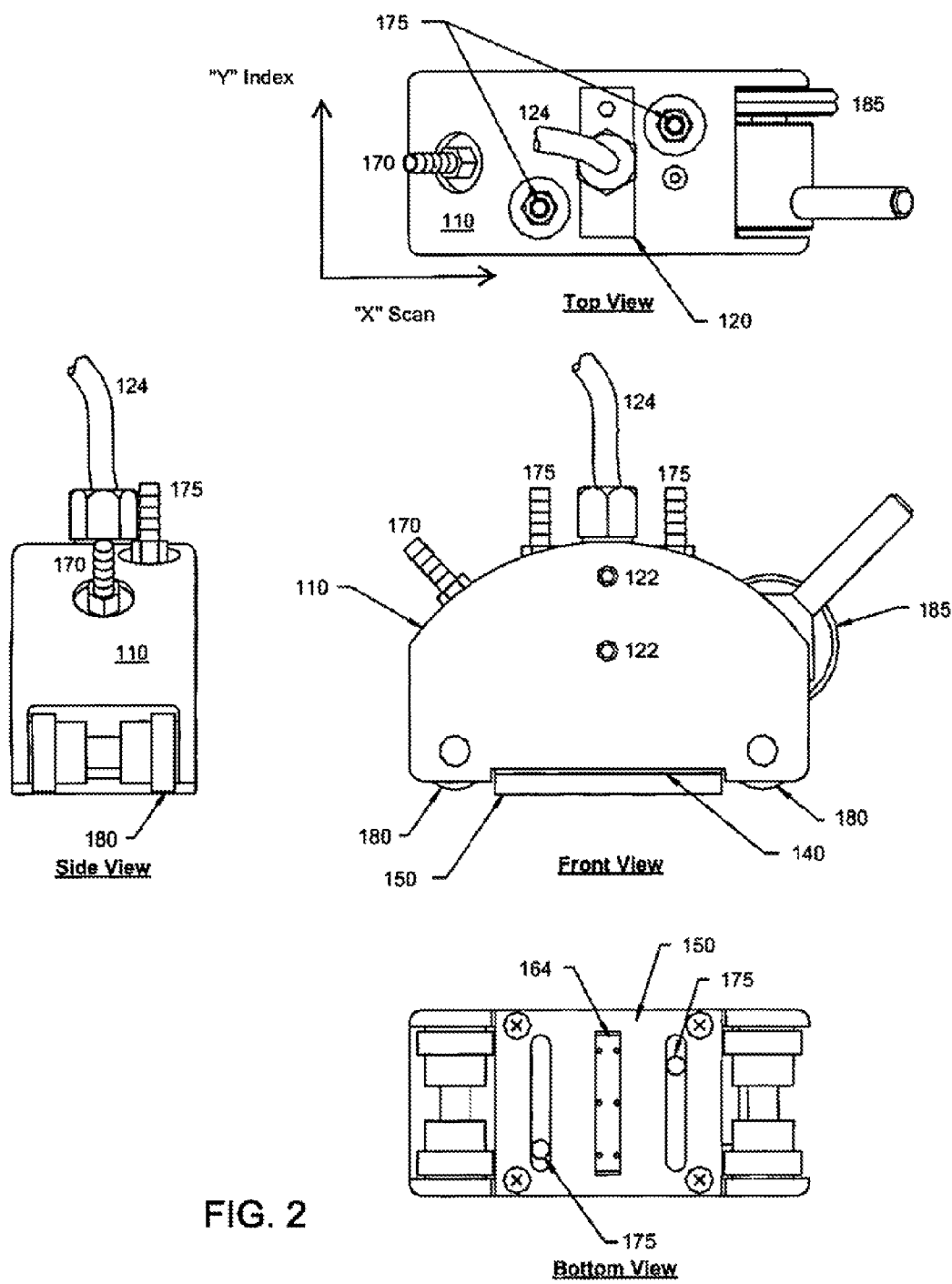
FIG. 2 is front, top, bottom and side views of the device of FIG. 1.
Figure 3:
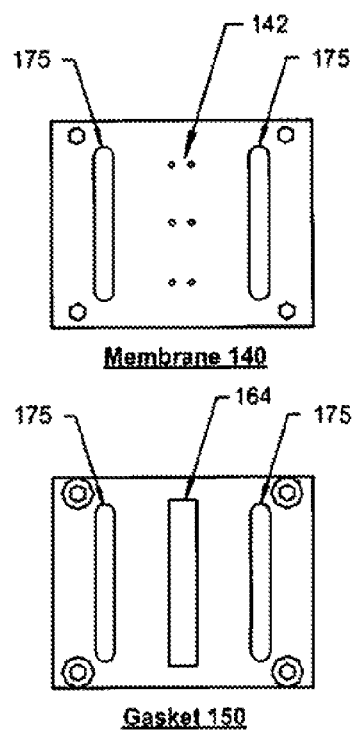
FIG. 3 is bottom views of the foam gasket and perforated membrane of the device of FIG. 1.

FIGS. 1-3 are various views of an example ultrasonic probe deployment device 100 according to the invention. The device is used to inspect material, which in this example is a bonded joint 195. The surface of the inspection area shall be referred to as the inspection surface 190. FIG. 1 is a cross-section view. FIG. 2 contains front, top, bottom and side views. FIG. 3 contains bottom views of the foam gasket and perforated membrane.

An ultrasonic probe 120 rests in a machined recess within the main housing 110 of the probe deployment device 100. Cable 124 is the transducer cable. Two set screws 122 located on each side of the device ensure that the probe 120 remains fixed within the housing 110. The height of the probe 120 can be adjusted vertically depending on the desired focal length of the ultrasonic probe, or (as illustrated) can be adapted to abut a shoulder 112 within the machined recess to set the stand-off distance of the probe to match it's focal length. In this example, the ultrasonic probe 120 is a phased array pulse-echo ultrasonic probe that makes a scan along the direction that is into and out of the paper in FIG. 1 (Y-direction). If an area scan is desired, the probe can be moved in the orthogonal direction (X-direction), which will be referred to as the scan direction. The Y-direction will be referred to as the index direction. As can be seen in the FIG. 2, "Top View" the device can be moved in the scan direction "X" to create an area scan by virtue of the fact that the phased array ultrasonic probe is made up of multiple ultrasonic transducer elements which have a scan width in the "Y" direction.

If the ultrasonic probe uses a single transducer that functions as both the transmitter and the receiver, a two-dimensional (X-Y) C-Scan can be produced by running the transducer in the X-direction while also incrementing the location of the scan lines in the Y-direction. Phased array ultrasonic probes contain a linear array of independent ultrasonic transducers in the Y-direction so that a single X-direction scan can produce an area mapping (paint brush approach) contributing to reducing the time required for inspecting an area. Phased array ultrasonic probes also provide for increased resolution and sensitivity compared to conventional spot probe transducers. Another advantage of embodiments of the invention is the use of what have become known in the art as "near-wall" ultrasonic probes which minimize the width of the device (e.g. dimension in the index direction) as this type of probe is adapted to have a minimum of dead space at ends of the probe array.

FIGS. 1-3 show the entire device, including the ultrasonic probe 120. The portion of the device without the ultrasonic probe 120 will be referred to as the ultrasonic probe support assembly. These assemblies can be designed for one specific ultrasonic probe 120 attached at one specific site on the assembly. Alternately, they can be designed for one specific probe, but with the possibility of attachment at different sites on the assembly. In yet another variation, they can be designed so that different types of ultrasonic probes can be attached.

The housing 110 in this non-limiting example is approximately 1.5" wide (i.e., measured along the index direction) by 3.5" long (i.e., measured along the scan direction). The overall small size enables the device to better negotiate complex geometries such as a tight radii and narrow flanges. Different sizes can accommodate different geometries. For example, an alternate design is 0.7" wide and 2.75" long. The housing is made of polycarbonate because it is durable, lightweight and is also translucent or equivalently transparent. The translucency allows visual inspection of the water column (described below), for example to verify that the water flow rate is sufficient to fill the water column and that no air bubbles or air pockets are present. This particular housing is constructed primarily from a single block of material. However, in alternate embodiments, the housing can be molded as a single piece or assembled from multiple pieces.

A perforated latex membrane 140 and polyurethane microcellular resilient foam (e.g. Poron®) gasket 150 (i.e. "foam gasket") are attached to the bottom side of the housing. These two components are shown in greater detail in FIG. 3 (which presents a simplified gasket design). The housing 110 and gasket 150 are shaped to form a cavity 160, which is filled with water. Note that, in this example, the cavity 160 is elongated along the index direction (into and out of the paper in FIG. 1) to accommodate the one-dimensional array of the ultrasonic probe. This volume of water will sometimes be referred to as a water column. The ultrasonic wave path 126 travels through this water column 160. In particular, the water column (and cavity) 160 includes the portion of the ultrasonic wave path 126 that interacts with the inspection surface. This area will be referred to as the inspection site 128. In this particular example, the water column includes the entire ultrasonic wave path 126 from transmitter to receiver (i.e., from probe 120 to the inspection site 128 and back).

The foam gasket 150 conforms to unevenness in the inspection surface 190 (e.g. spot welds), which can be recessed or protruding. The foam gasket 150 also conforms to inspection articles having curvature. Thus, it provides a seal around the inspection site to prevent (or at least reduce) water from escaping the water column 160. The gasket 150 is foam in this design, but can be made of other materials (e.g., rubber) or using other designs. Typically, the gasket material will be compressible and resilient in order to allow the following of contours and unevenness. The gasket typically will be made of materials that are resistant to abrasion and chemical degredation, for example, by water and/or oils.

In FIG. 1 the gasket 150 extends beyond the roller guides 180 by a preload offset 152 (e.g. a predetermined gap). At rest, i.e. at times when device 100 may not be obtaining ultrasonic scans of the surface 190, the roller guides are not in contact with the inspection surface 190. In a typical operation (e.g. during a scan) a downward force is applied to the device 100 to compress gasket 150 against the inspection surface 190 and bring the roller guides 180 into contact with the surface. In embodiments of the invention, it can be beneficial to design the size of the preload offset 152 to obtain a desired amount of compression of the gasket 150 to optimize seal integrity, which has been found in applications to contribute greatly to minimizing water loss. In this particular design, the gasket 150 is 0.125" thick.

The ultrasonic probe support assembly can be designed to navigate over tightly contoured surfaces and/or over rough surfaces. This particular design can be designed to inspect over contours that could be as small as 1" diameter curves. The gaskets and wheel sizes/positioning can be designed to accommodate a wide range of out-of-flatness surfaces (local undulations). The gasket can also be designed to be thicker and more compressible (e.g. more compliant) to allow the device to navigate over larger local bumps (e.g. weld remnants) that might be as large as 0.25" above the normal, flat surface. Other conformable seals besides foam gaskets can also be used. Neoprene, silicone, Teflon, polyamide films, soft plastics, vinyl, sponge, and pleated accordion structures are some examples of alternate materials and/or designs. In practice the microcellular foam gasket has been found to be preferable in that it provides for greatly reduced water leakage onto the inspection surface as compared to for example, bristle or brush type gaskets. The polyurethane microcellular foam gasket used in the present example includes an open cell foam layer sandwiched between abrasive and oil resistant layers for contacting the inspection surface, and can also include an adhesive layer for attachment to the housing 110.

The perforated membrane 140 divides the cavity 160 into two chambers, which will be referred to as the non-contact chamber 162 and the contact chamber 164. The contact chamber 164 includes the inspection site 128 (i.e., is in "contact" with the inspection surface). The non-contact chamber 162 does not include the inspection site. The non-contact chamber 162 preferably is larger in volume than the contact chamber 164 and holds the majority of the water. In addition, the ultrasonic wave path preferably is longer in the non-contact chamber than in the contact chamber. An angled inlet port 170 enables the continuous supply of water to the water column 160 (specifically, to the non-contact chamber 162). The water can be provided from an external source or can be recirculated to a self-contained reservoir. Several small holes 142 (see FIG. 3) located outside of the ultrasonic wave path 160 permit water to flow from the non-contact chamber 162 to the contact chamber 164.

The membrane 140 helps to prevent water from rushing out of the probe deployment device and thus also helps to prevent air from entering the cavity 160. The majority of water is contained in the non-contact chamber 162, which is better confined (i.e., less leaky) than the contact chamber 164. This can be important when the probe deployment device is transferred from one inspection article to another. Without the membrane 140, the entire water column 160 would be lost during the transfer and would have to be re-established after the transfer. With the membrane 140, only the water in the contact chamber 164 is lost and re-established. The membrane 140 preferably is thin and of low acoustic impedance comparable to that of water so that the ultrasonic waves pass through the membrane with little attenuation.

Other membrane 140 designs are possible. The perforations 142 placed in the membrane 140 can be varied to accommodate different flow rates of water through the cavity 160. Materials other than latex can be used, for example nitrile, vinyl, cellophane (tape) and PTFE. In an alternate approach, the membrane is permeable not because it contains perforations, but because the material itself is porous, such as gels or screens with very small openings.

Vacuum ports 175 extend to the inspection surface forward and aft of the inspection site 128, to enable the continuous collection of excess water on the inspection surface. The location of vacuum ports 175 on both sides of the inspection site 128 support the collection of excess water regardless of the direction of motion of the probe deployment device, thus leaving the inspection article relatively dry after the inspection. In addition, the collected excess water can then be reused to supply the water column. By locating vacuum ports 175 fore and aft of the inspection site within the device body, i.e. not to the sides, the width of the device can be minimized thus facilitating the inspection of narrow joint/bonds.

Four wheels 180 facilitate the movement of the probe deployment device over the inspection article. In this example, they are located at the outboard edges of the probe deployment device to avoid contact with surface irregularities (e.g., spot welds) which could potentially lift the device from the inspection surface and disrupt the water column within the gasket. By locating wheels 180 fore and aft of the inspection site within the device body, i.e. not to the sides, the width of the device can be minimized thus facilitating the inspection of narrow joint/bonds.

A water-proof encoder 185 contacts the rear wheel 180 to synchronize the probe deployment device movement with the ultrasonic data acquisition. In addition to tracking the displacement of the probe, the encoder information can also be used to dimension or size flaws. A resulting C-Scan inspection image can then be generated. Other encoders can also be used. Examples include direct linear encoders such as potentiometer or linear variable differential transformers (LVDT), string encoders including those based on potentiometers or rotary encoders or other principles, and non-contact encoders such as those based on laser Doppler velocimetry sensors and laser interferometry.

Figure 8:
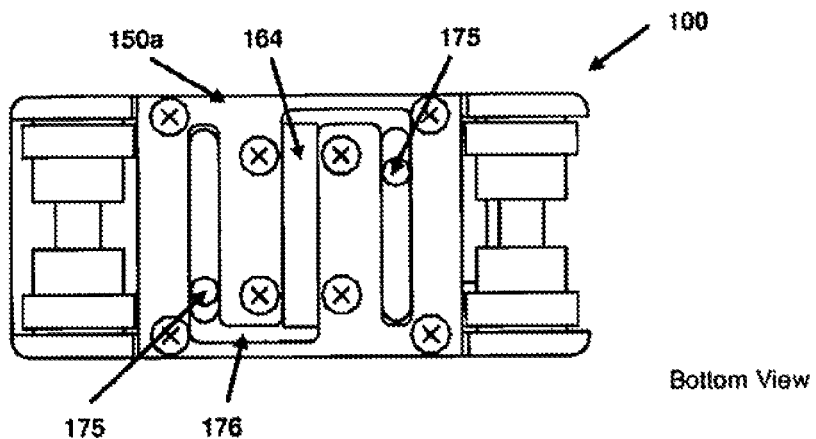
FIG. 8 presents alternative embodiments of probe deployment sealing gaskets, according to the invention.
Figure 8:
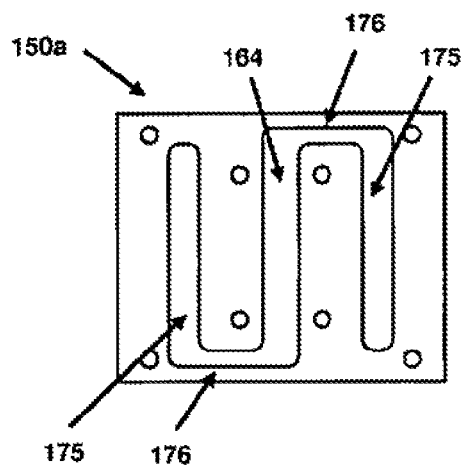
Figure 8:
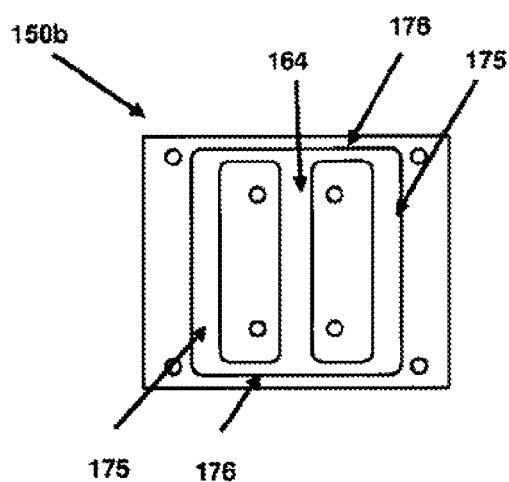

FIG. 8 presents alternative embodiments of probe deployment sealing gaskets, according to the invention. FIG. 8 shows a bottom view of a probe deployment device 100 with an alternative embodiment of a sealing gasket 150a. The gasket designs presented in FIG. 8 have been found to allow for a controllable (e.g. reduced) fluid flow from the contact chamber 164 to the vacuum ports 175, thereby reducing fluid consumption and turbulence within the device. Reduced turbulence improves the fidelity of the ultrasonic inspection signal. Gasket 150a includes a passageway 176 (e.g. slot(s)) providing a fluidic connection from the contact chamber 164 to the vacuum ports 175. It has been found that this configuration, referred to as an "S" shaped gasket, is well suited to the inspection of bonded flanges that are narrower than the probe deployment device. The conductance of the passageway 176 can be varied through control of it's physical dimensions to allow balancing the flow of water into the device and out through the vacuum ports, thereby minimizing loss and consumption of water during an inspection. Gasket 150b is another alternative embodiment that has been found to be well suited to the inspection of bonded flanges that are wider than the probe deployment device. Gasket 150b is referred to as a "figure 8" shaped gasket. Again passageways 176 are provided for connecting the contact chamber 164 to the vacuum ports 175.

The ultrasonic probe deployment device described above has many advantages as described in the following (not all implementations will have all of the listed features). For example, ultrasonic coupling is typically achieved by applying a gel to the inspection surface or by continuously spraying water on the surface. Gels are messy, not useable on some surfaces and can move away from the inspection area as the probe moves across the surface. Continuously spraying water or other non-viscous liquids can also be messy, and the liquids may flow away from the inspection site or puddle at low spots. This can result in marginal signal transmission or even complete signal drop-out (loss of ultrasonic coupling) during the inspection. Such non-optimum signals may not be obvious to the inspector and, as a result, poor data or inaccurate data may be used to assess the integrity of the item being inspected. The device described in the above example overcomes those limitations by providing a continuous, uniform and reliable water column to couple the ultrasonic wave between the inspection surface and the ultrasonic probe. The resulting inspections are of higher quality and can be completed faster than current alternatives.

The device can negotiate uneven surfaces caused by spot welds and or spot weld expulsions as well as complex curvature and geometry while maintaining optimum (ideal) water coupling and ultrasonic sound wave transmission. The vacuum ports collect excess water. This leaves the inspection article relatively dry post inspection. The collected excess water can also be reused to supply the water columns (for closed systems). The device can be transferred from one inspection article to another without significant loss of water coupling from the water column directly below the ultrasonic probe. Otherwise the water column would have to be reestablished, which would delay the inspection of the second inspection article.

Furthermore, probe placement within the housing can be adjusted to optimize the distance between the inspection site and the ultrasonic probe. This adjustment allows users to accurately and repeatably focus the ultrasonic waves at a particular depth/region for maximum sensitivity and resolution. The position encoder synchronizes movement of the device with the ultrasonic data acquisition, thus allowing the generation of area images (e.g., C-Scan inspection images). These images are generally easier for a field inspector to interpret compared to A or B-Scan ultrasonic signals. This also facilitates the location and sizing of flaws.

Figure 4:
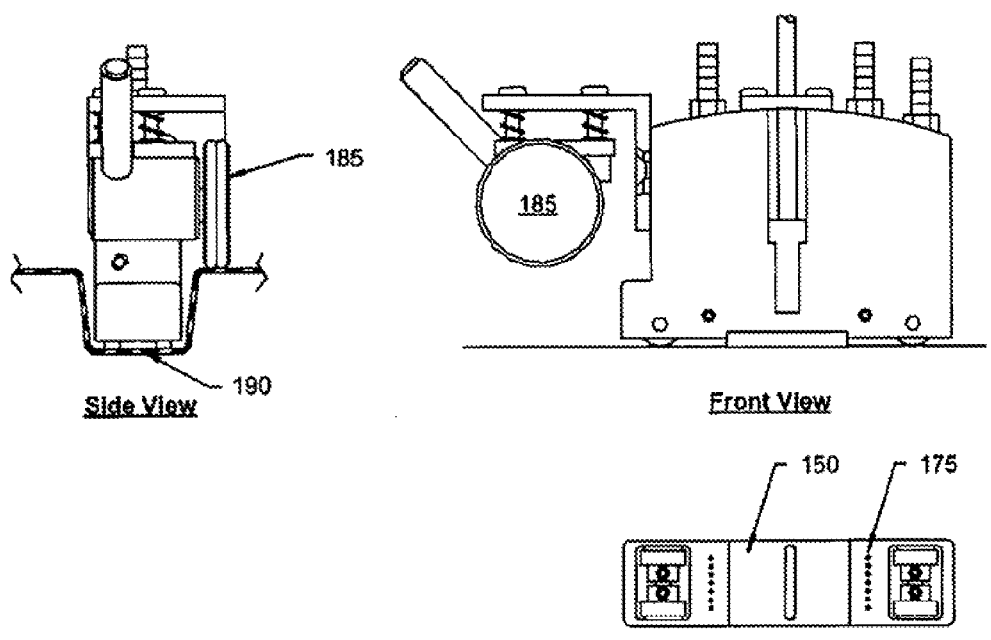
FIG. 4 is front, bottom and side views of another ultrasonic probe deployment device according to the invention, with an offset encoder.

FIGS. 4-7 illustrate variations of devices according to the present invention. Many of these figures are simplified for purposes of clarity. In FIG. 4, the device is designed for scanning deep, narrow valleys 190. As a result, the encoder 185 is offset to a position outside the valley 190 and directly contacts the surface (as opposed to contacting one of the wheels 180 as in FIGS. 1-3). In addition, as shown in the bottom view, the vacuum ports 175 are now located outside the gasket 150.

Figure 5A:
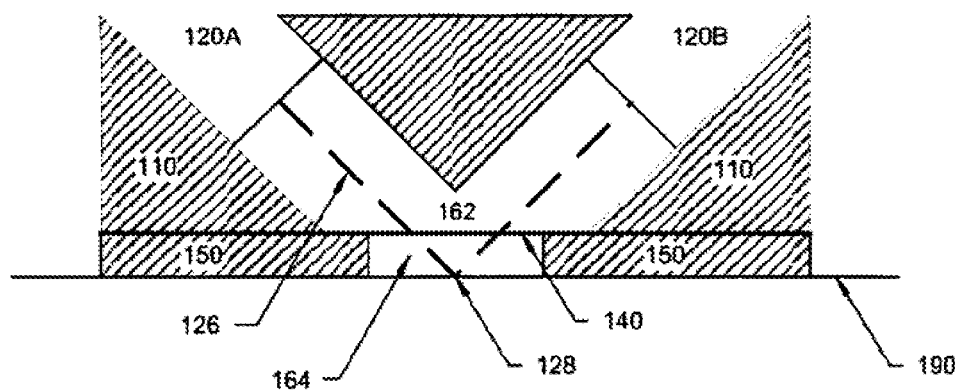
FIGS. 5A-5C are simplified cross-section views of additional ultrasonic probe deployment devices, for use with pitch-catch ultrasonic probes.
Figure 5B:
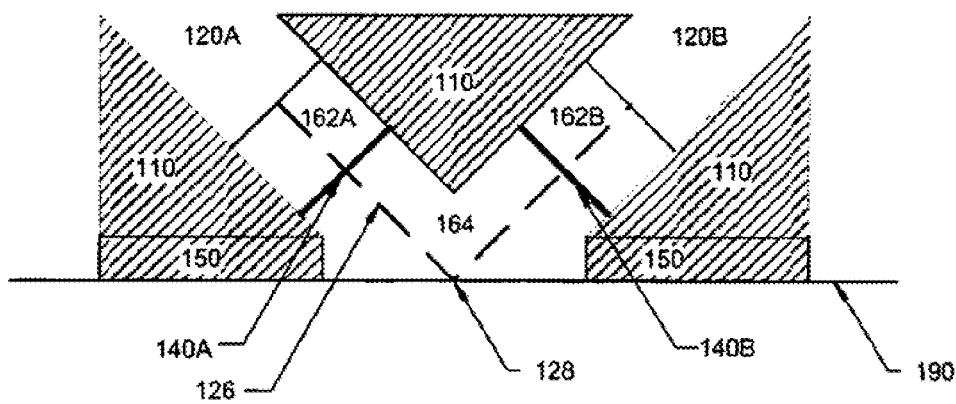
Figure 5C:
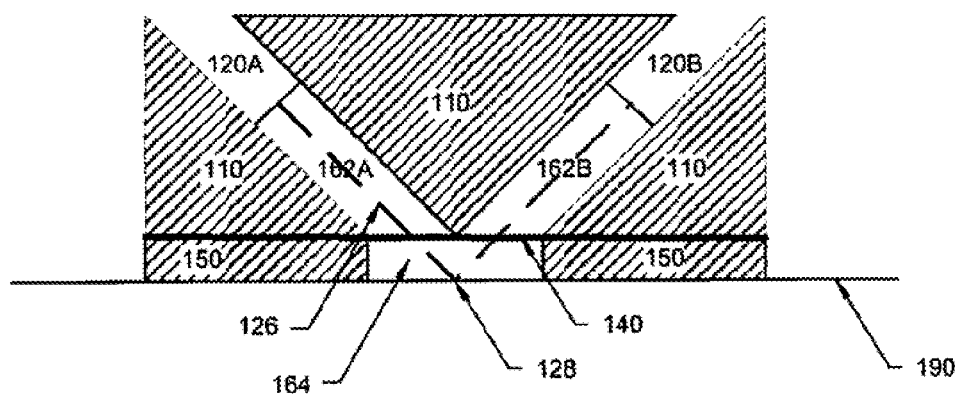

In FIGS. 5A-5C, there are two ultrasonic probes arranged in a pitch-catch configuration. One probe 120A acts as the transmitter and the other probe 120B acts as the receiver. The cavity 160 in this example is "V"- or "Y"-shaped. In FIG. 5B, two separate membranes 140A and 140B are used. In FIG. 5C, the non-contact chamber 162 is divided into two parts 162A and 162B.

In conventional pulse-echo ultrasonics, pulses of high frequency sound waves are introduced into a structure being inspected. A-Scan signals represent the response of the stress waves, in amplitude and time, as they travel through the material. As the waves interact with defects or flaw interfaces within the solid and portions of the pulse's energy are reflected back to the transducer, the flaws are detected, amplified and displayed. The interaction of the ultrasonic waves with defects and the resulting time vs. amplitude signal depends on the wave mode, its frequency and the material properties of the structure. Flaw size can be estimated by comparing the amplitude of a discontinuity signal with that of a signal from a discontinuity of known size and shape. Flaw location (depth) can be determined from the position of the flaw echo along a calibrated time base.

In pitch-catch ultrasonics, one probe introduces a pressure wave into the specimen and a second probe detects the transmitted wave. A complex wave front is generated internally in the material as a result of velocity characteristics, acoustical impedance, and thickness. The time and amount of energy is affected by the changes in material properties, such as thickness, disbonds, and discontinuities. The mechanical vibration (ultrasound) is introduced into the specimen through a couplant and travels by wave motion through the specimen at the velocity of sound. If the pulses encounter a reflecting surface, some or all of the energy is reflected and monitored by the probe. The reflected beam, or echo, can be created by any normal or abnormal (flaw) interface. Complete reflection, partial reflection, scattering, or other detectable effects on the ultrasonic waves can be used as the basis of flaw detection.

Figure 6:
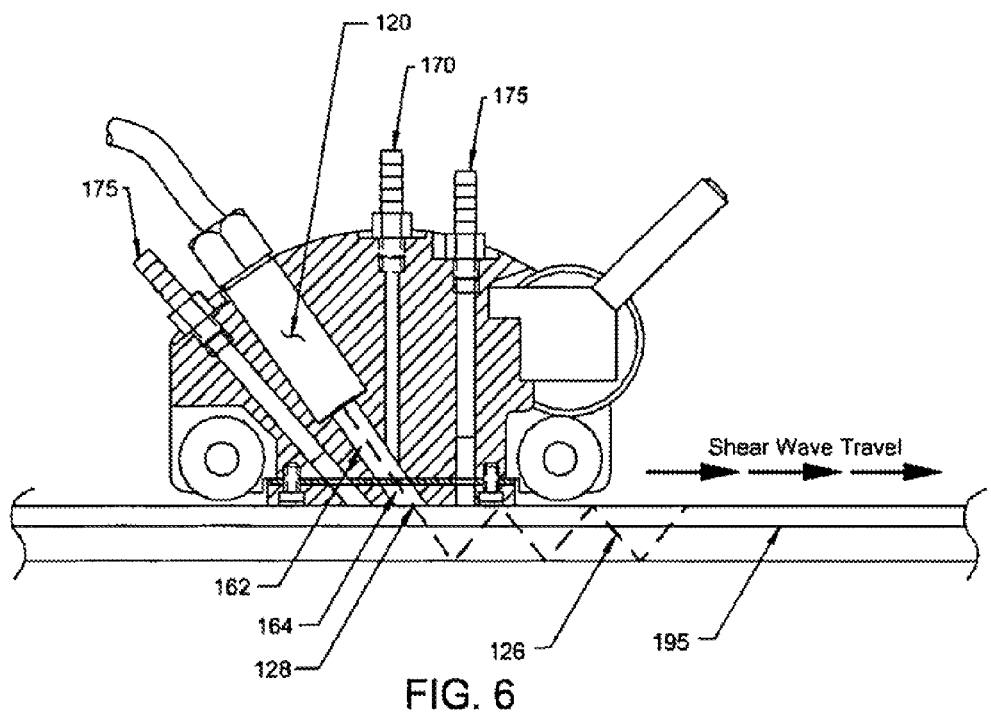
FIG. 6 is a cross-section view of a pitch-catch ultrasonic probe deployment device according to the invention.

FIG. 6 is a cross-section view of a pitch-catch ultrasonic probe deployment device. In this example, the ultrasonic probe 120 is housed in the probe deployment device at an angle relative to the inspection surface. The probe 120 produces an ultrasonic wave 126 that travels at an angle. Thus, shear wave inspection can be performed. The shear wave inspection can be in a pulse-echo mode where the probe acts as both the transmitter and receiver. FIG. 6 shows operation in a pitch-catch mode where probe 120 acts as the transmitter and another probe (not shown in FIG. 6) acts as the receiver. The receiver probe could be stationary or could move with probe 120. For example, the receiver probe could be contained in a second device that is yoked to the first device. The shear wave could inspect all of the material between the two transducers. If the adhesive bond 195 is intact, the ultrasonic wave will pass unobstructed to the receiver probe.

Disband and delamination detection can also be achieved by taking the A-Scan signals and transforming them into a single C-Scan image of the part being inspected. C-Scan technology uses information from single point A-Scan waveforms to produce an area mapping of the inspection surface. These two-dimensional images can be produced by digitizing point-by-point signal variations of an interrogating sensor while it is scanned over a surface. C-Scan area views provide the inspector with easier-to-use and more reliable data with which to recognize flaw patterns. This format provides a quantitative display of signal amplitudes or time-of-flight data obtained over an area. The X-Y position of flaws can be mapped and time-of-flight data can be converted and displayed by image processing equipment to provide an indication of flaw depth. A variety of PC-based manual and automated scanning devices can provide position information with digitized ultrasonic signals. Specific emphasis can be placed on portions of the ultrasonic signal and highlighted in a color-mapped C-Scan, based on user specified amplitude gates, time-of-flight values and signal waveforms.

Alternate embodiments can be based on spot probe, which represents a single transducer. The spot probe can be scanned in the X and Y directions to produce a C-Scan image. A linear array probe can be thought of as a number of single, miniaturized spot probes all arranged in a line and placed in one housing (house paint brush vs. artist's single paint brush). Thus, if the array probe is moved across a surface it can generate a C-Scan that is as wide as the probe. The probe deployment device can be adapted to hold either a single ultrasonic spot probe or a multi-element ultrasonic array probe.

Various modalities can also be used. Examples of pulse-echo, pitch-catch, longitudinal waves and shear waves were described above. In addition, another type of ultrasonic wave is the Lamb wave. The Lamb wave can be introduced in a number of ways. Wave mode conversion can occur at changes within the structure.

Figure 7:
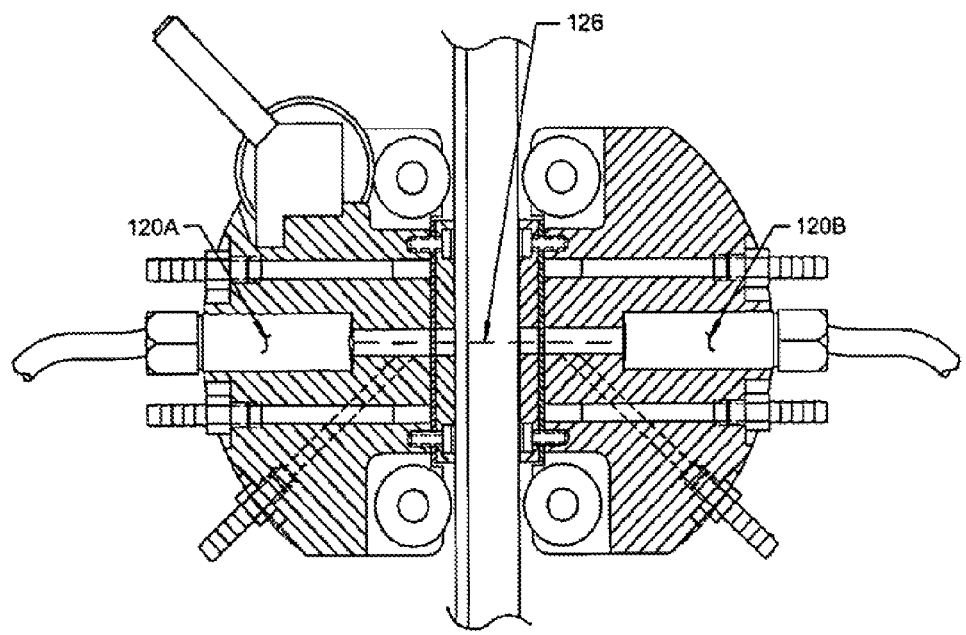
FIG. 7 is a cross-section view illustrating two-sided inspection.

The device can also be adapted for two sided (back-sided) inspections. In FIG. 7, two devices are used, one placed on each side of the structure to be inspected. The two devices move together (e.g., using a yoke arrangement) so that the two probes 120A-B are aligned with each other. The wave path 126 goes from one probe 120A, through the material being inspected, to the other probe 120B. One advantage is that the inspections are done in through-transmission mode so that the signal need only pass through the part once. There is less attenuation and stronger signals from which to ascertain the presence of small flaws.

In another variation, the ultrasonic probe is stationary and the part being inspected is moved pass the ultrasonic probe. For example, the ultrasonic probe may be held in a relatively stationary position while parts on an assembly line travel past the probe.

The inspection surface 190 also is not required to be a horizontal surface, for example as shown in FIG. 7. The probe device is designed for different orientations, including vertical surfaces (e.g., door panels), slanted surfaces, or even upside down (e.g., the interior of an automobile roof surface). In the examples described above, the "bottom" of the probe device usually faces down. However, more generally, the terms "bottom" and "bottom side" of the housing are meant to refer to the side facing the inspection surface, regardless of the physical orientation of that surface.

Finally, although the example above was described in the context of inspecting adhesive bonds on automobiles, the invention is not limited to this application. Aircraft joint, both composite and metallic, can also be inspected. In general, the approaches described above can be applied to any material and structural configuration that lends itself to ultrasonic inspections (e.g. composite materials, metallic structures, ceramics, concrete). Other examples include the inspection of various joining methods: resistance spot welds, friction stir welds, self-piercing rivets and clinch joining to name a few. Ultrasonic inspection can also be used for surface indentation/cosmetic quality of surfaces, leak testing by looking for breaks in a seal, and acoustic testing in the form of looking for coupling between surfaces.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

What is claimed is:

1. A portable ultrasonic probe deployment device for inspecting material located on an inspection surface, the device comprising:
 a housing;
 an ultrasonic probe attached to the housing;
 a conforming seal attached to a bottom side of the housing and conforming to the inspection surface, the conforming seal forming a seal around the inspection site;
 a cavity created within the housing and the seal, the cavity extending along a portion of an ultrasonic wave path that includes the inspection site;
 a permeable membrane attached to the bottom side of the housing between the housing and the seal, the permeable membrane dividing the cavity into a non-contact chamber contained by the housing and a contact chamber contained by the seal;
 a water supply port connected to the non-contact chamber for supplying water to the non-contact chamber, the permeable membrane permitting flow of water from the non-contact chamber to the contact chamber.

2. The device of claim 1, further comprising:
 roller guides attached to the housing for facilitating movement along a scan direction transverse to the index direction.

3. The device of claim 1, further comprising:
 a position encoder attached to the housing, for encoding a position of the device along the scan direction.

4. The device of claim 1, further comprising:
 one or more vacuum ports extending to the inspection surface for removing excess water from the inspection surface.

5. The device of claim 4, wherein the one or more vacuum ports are disposed proximal to the fore and aft ends of the housing, and not disposed along lateral sides of the housing.

6. The device of claim 1, wherein the conforming seal comprises a passageway, the passageway operationally configured to allow a flow of fluid between the contact chamber and the one or more vacuum ports.

7. The device of claim 1, wherein the ultrasonic probe comprises a near wall ultrasonic probe.

8. The device of claim 2, wherein the roller guides and the conforming seal are operationally configured to have a preload offset, the preload offset providing for a desired amount of compression of the conforming seal.

9. The device of claim 1 wherein the permeable membrane is a membrane constructed of non-porous material with perforations.

10. The device of claim 1 wherein the permeable membrane is a perforated membrane.

11. The device of claim 1 wherein the housing is a translucent housing.

12. The device of claim 1 wherein the conforming seal is a polyurethane foam gasket.

13. The device of claim 1 wherein the conforming seal is a rubber gasket.

14. The device of claim 1 wherein the encoder comprises a two-dimensional position encoder for encoding a position of the device along both the scan and index directions.

15. The device of claim 1 wherein the ultrasonic probe is attached to the housing with an adjustable attachment operatively arranged to allow adjusting a standoff height of the ultrasonic probe from the inspection surface.

16. An ultrasonic probe support assembly for use in inspecting material located on an inspection surface, the support assembly comprising:
- a housing;
- an ultrasonic probe attached to the housing;
- a conforming seal attached to a bottom side of the housing and conforming to the inspection surface, the conforming seal forming a seal around the inspection site;
- a cavity created within the housing and the seal, the cavity extending along a portion of an ultrasonic wave path that includes the inspection site;
- a permeable membrane attached to the bottom side of the housing between the housing and the seal, the permeable membrane dividing the cavity into a non-contact chamber contained by the housing and a contact chamber contained by the seal;
- a water supply port connected to the non-contact chamber for supplying water to the non-contact chamber, the permeable membrane permitting flow of water from the non-contact chamber to the contact chamber.

17. The device of claim 16, further comprising:
- roller guides attached to the housing for facilitating movement along a scan direction transverse to the index direction.

18. The device of claim 16, further comprising:
- a position encoder attached to the housing, for encoding a position of the device along the scan direction.

19. The device of claim 16, further comprising:
- one or more vacuum ports extending to the inspection surface for removing excess water from the inspection surface.

20. The device of claim 19, wherein the one or more vacuum ports are disposed proximal to the fore and aft ends of the housing, and not disposed along lateral sides of the housing.

21. The device of claim 16, wherein the conforming seal comprises a passageway, the passageway operationally configured to allow a flow of fluid between the contact chamber and the one or more vacuum ports.

22. The device of claim 17, wherein the roller guides and the conforming seal are operationally configured to have a preload offset, the preload offset providing for a desired amount of compression of the conforming seal.

23. The device of claim 16, wherein the permeable membrane is a membrane constructed of non-porous material with perforations.

24. The device of claim 16, wherein the permeable membrane is a perforated membrane.

25. The device of claim 16, wherein the housing is a translucent housing.

26. The device of claim 16, wherein the housing is a polycarbonate housing.

27. The device of claim 16, wherein the conforming seal is a polyurethane foam gasket.

28. The device of claim 16, wherein the conforming seal is a rubber gasket.

29. The device of claim 18, wherein the position encoder comprises a two-dimensional position encoder, for encoding a position of the device along both the scan and index directions.

30. The device of claim 16, further comprising an adjustable attachment attached to the housing to allow adjusting a standoff height of an ultrasonic probe from the inspection surface.

* * * * *